United States Patent
Ely

(10) Patent No.: US 9,814,625 B2
(45) Date of Patent: Nov. 14, 2017

(54) SELECTIVE ATTENUATING EARPLUG

(71) Applicant: 3M INNOVATIVE PROPERTIES COMPANY, St. Paul, MN (US)

(72) Inventor: Jacob Ely, Indianapolis, IN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 330 days.

(21) Appl. No.: 13/734,268

(22) Filed: Jan. 4, 2013

(65) Prior Publication Data

US 2014/0190494 A1 Jul. 10, 2014

(51) Int. Cl.
*A61F 11/06* (2006.01)
*A61F 11/08* (2006.01)
*A61F 11/12* (2006.01)

(52) U.S. Cl.
CPC .............. *A61F 11/12* (2013.01); *A61F 11/08* (2013.01); *A61F 2011/085* (2013.01); *A61F 2250/0004* (2013.01); *A61F 2250/0069* (2013.01)

(58) Field of Classification Search
CPC .......... A61F 11/00; A61F 11/06; A61F 11/08; A61F 11/045; A61F 2011/085; A61F 11/10; A61F 11/12; A61F 11/14; H04R 25/02; F16K 31/00; F16K 35/00; F16K 5/07; F16K 5/00; F16K 31/524; F16K 31/563; F16K 31/566
USPC .................. 128/864, 866–868; 381/328, 380; 181/130–131, 135; 251/101, 107–108, 251/352, 251, 259, 297, 304, 309, 313, 251/75
See application file for complete search history.

(56) References Cited

U.S. PATENT DOCUMENTS

| | | | |
|---|---|---|---|
| 4,916,758 A * | 4/1990 | Jordan-Ross | A45D 44/12 128/866 |
| 4,974,606 A | 12/1990 | Van Mierlo | |
| 5,957,136 A | 9/1999 | Magidson | |
| 5,983,399 A * | 11/1999 | Falco | A61F 11/12 128/864 |
| 6,068,079 A | 5/2000 | Hamery | |
| 6,070,693 A | 6/2000 | Hamery | |
| 6,082,485 A | 7/2000 | Smith | |
| 6,148,821 A | 11/2000 | Falco | |
| 6,286,622 B1 | 9/2001 | Tiemann | |
| 6,440,339 B1 * | 8/2002 | Magidson | A61F 11/08 264/157 |
| 6,768,804 B1 | 7/2004 | Isvan | |
| 7,025,061 B2 | 4/2006 | Haussmann | |

(Continued)

FOREIGN PATENT DOCUMENTS

| | | | |
|---|---|---|---|
| AU | 56067-73 | * | 11/1974 |
| AU | 5606773 | | 11/1974 |

(Continued)

OTHER PUBLICATIONS

3M Occupational Health & Environmental Safety Division, "3M™ Combat Arms Earplugs," 2 pages, © 3M™ 2010.

(Continued)

*Primary Examiner* — Kari Rodriquez
*Assistant Examiner* — Camtu Nguyen

(57) ABSTRACT

A selective attenuating earplug is provided. In an exemplary embodiment, a selective attenuating earplug includes a switch adjustable between a first position and a second position, and the switch includes at least one cantilever spring arm.

13 Claims, 3 Drawing Sheets

(56) References Cited

U.S. PATENT DOCUMENTS

| | | | |
|---|---|---|---|
| 7,182,087 B1* | 2/2007 | Marsh | A61F 11/08 128/864 |
| 7,401,680 B2 | 7/2008 | Kurth | |
| 7,512,243 B2* | 3/2009 | Haussmann | A61F 11/08 381/380 |
| 7,634,099 B2 | 12/2009 | Harvey | |
| 8,161,975 B2 | 4/2012 | Turdjian | |
| 2006/0042868 A1* | 3/2006 | Berg et al. | 181/135 |
| 2006/0045297 A1* | 3/2006 | Haussmann | A61F 11/08 381/322 |
| 2008/0276945 A1 | 11/2008 | Rosen | |
| 2010/0294285 A1* | 11/2010 | Turdjian | A61F 11/08 128/867 |
| 2011/0158421 A1 | 6/2011 | Voix | |
| 2013/0152949 A1* | 6/2013 | Simon | A61F 11/08 128/868 |

FOREIGN PATENT DOCUMENTS

| | | |
|---|---|---|
| DE | 4 217 043 | 5/1991 |
| EP | 0955025 | 11/1999 |
| EP | 1 629 802 | 3/2006 |
| GB | 1 276 498 | 8/1968 |
| JP | 08 037697 | 7/1994 |
| JP | 2009172270 | 1/2008 |
| WO | WO 2009046170 | 4/2009 |
| WO | WO 2009/086649 | 7/2009 |
| WO | WO 2012/149970 | 11/2012 |

OTHER PUBLICATIONS

International Application PCT/US2013/076441 Search Report dated Mar. 28, 2014.

* cited by examiner

SELECTIVE ATTENUATING EARPLUG

TECHNICAL FIELD

This invention relates to a selective attenuating earplug having a switch, in particular a selective attenuating earplug having a switch comprising one or more cantilever spring arms.

BACKGROUND

The use of hearing protective and noise attenuating devices are well known, and various types of devices have been considered. Such devices include earplugs and semi-aural devices partially or completely constructed of foam or rubber materials that are inserted into, or placed over, the ear canal of a user to physically obstruct the passage of sound waves into the inner ear.

Environmental sounds are typically comprised of a mixture of various sound wave frequencies having varying intensities. Selective attenuating earplugs may be provided that allow a wearer to select from multiple performance settings. For example, a low sound attenuating mode may be selected to attenuate impulse noise, such as from a gunshot, while allowing voices or warning signals to pass through to the ear canal of a wearer. A high attenuating mode may be selected to attenuate all sound regardless of intensity. Various selective attenuating earplugs are available, such as COMBAT ARMS earplugs available from 3M Co. of St. Paul, Minn. For example, dual-ended COMBAT ARMS include first and second ends that may be at least partially inserted into an ear canal of a user. Insertion of a first end may provide attenuation of high-impulse noise, while insertion of a second end may provide maximum attenuation. Single-ended COMBAT ARMS earplugs include a rocker cover, for example, that may be switched between an open and closed position. When in an open position, sound is allowed to enter a sound channel of the earplug and pass through a filter that restricts high-impulse noise before entering the ear canal. When the rocker cover is closed, maximum attenuation may be provided for sound at any level.

SUMMARY

In an exemplary embodiment, a selective attenuating earplug is provided that includes a tip having a first end and a second end, a body attached to the tip, an acoustic channel extending from a first end of the tip to an aperture of the body, and a switch adjustable between a first position in which the aperture is at least partially open to allow passage of sound through the aperture and the acoustic channel and a second position in which the aperture is blocked. The switch comprises a first cantilever spring arm including a shape that interacts with a feature on a surface of the body, and the shape is biased against the feature on the surface of the body to maintain the switch in the first position or the second position. In some embodiments, the first cantilever spring arm includes a protrusion that interacts with a first recess on the surface of the body to maintain the switch in the first position and interacts with a second recess on the surface of the body to maintain the switch in the second position.

In another exemplary embodiment, a selective attenuating earplug is provided that includes a sound attenuating tip having a first end and a second end, a body coupled to the sound attenuating tip, an acoustic channel extending from a first end of the sound attenuating tip to an aperture of the body, and a switch comprising a first cantilever spring arm having a sealing pad, the switch adjustable between a first position in which the aperture is at least partially open to allow passage of sound through the aperture and the acoustic channel and a second position in which the aperture is blocked by the sealing pad. The first cantilever spring arm biases the sealing pad towards the aperture in a first position and towards a surface of the body in a second position.

In a further embodiment, a hearing protection device is provided that includes first and second selective attenuating earplugs joined by a cord, wherein each of the first and second selective attenuating earplugs comprise a tip having a first end and a second end, a body attached to the tip, an acoustic channel extending from a first end of the tip to an aperture of the body, and a switch adjustable between a first position in which the aperture is at least partially open to allow passage of sound through the aperture and the acoustic channel and a second position in which the aperture is blocked. The switch comprises a first cantilever spring arm including a shape that interacts with a feature on a surface of the body, and the shape is biased against the feature in the surface of the body to maintain the switch in the first position or the second position.

The above summary of the present invention is not intended to describe each disclosed embodiment or every implementation of the present invention. The Figures and the Detailed Description, which follow, more particularly exemplify illustrative embodiments.

BRIEF DESCRIPTION OF DRAWINGS

The present invention will be further explained with reference to the appended Figures, wherein like structure is referred to by like numerals throughout the several views, and wherein.

While the above-identified figures set forth various embodiments of the disclosed subject matter, other embodiments are also contemplated. In all cases, this disclosure presents the disclosed subject matter by way of representation and not limitation. It should be understood that numerous other modifications and embodiments can be devised by those skilled in the art which fall within the scope and spirit of the principles of this disclosure.

DETAILED DESCRIPTION

The present disclosure provides a selective attenuating earplug that may be switched between multiple operating modes to adjust the performance of the earplug. The selective attenuating earplug provides at least a first mode that may allow sound having a specified frequency or intensity to pass to the ear canal of a wearer with little or no attenuation while attenuating sounds in a different frequency or intensity range, and a second mode providing a maximum level of attenuation across a certain frequency and/or intensity range. The selective capability of the earplug allows a wearer to select the degree of desired sound attenuation depending on the current environment surrounding the wearer. A selective attenuation mode may be selected when a wearer desires to hear intelligible speech or warning signals in a noisy environment, for example, while still being protected from dangerous noises. Such a mode may be particularly desirable when the noisy environment includes gun shots, loud industrial noises, and the like. A maximum attenuation mode may be selected to minimize most sounds throughout the frequency range from entering an ear canal, regardless of intensity.

Figure 1:
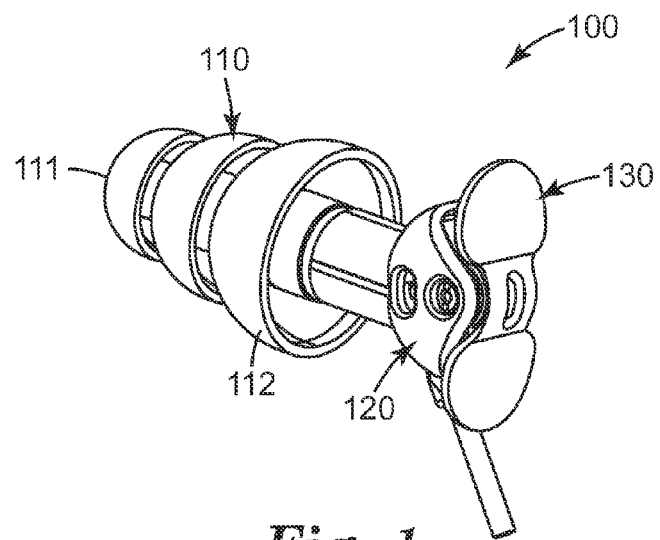
FIG. 1 is a perspective view of a selective attenuating earplug according to an exemplary embodiment of the present invention.

Referring to FIG. 1, an exemplary selective attenuating earplug 100 according to the present disclosure includes a tip 110, such as a sound attenuating tip, having a first end 111 and a second end 112. Earplug 100 further includes a body 120 attached to tip 110, and an acoustic channel (not shown) extending from a first end of tip 110 to an aperture of the body. Switch 130 is adjustable between a first position in which sound is allowed to pass through the aperture and acoustic channel and a second position in which the aperture is blocked. As will be described further herein, an exemplary switch 130 includes one or more cantilever spring arms that interact with one or more features of body 120 to maintain the switch in a desired position.

Figure 2:
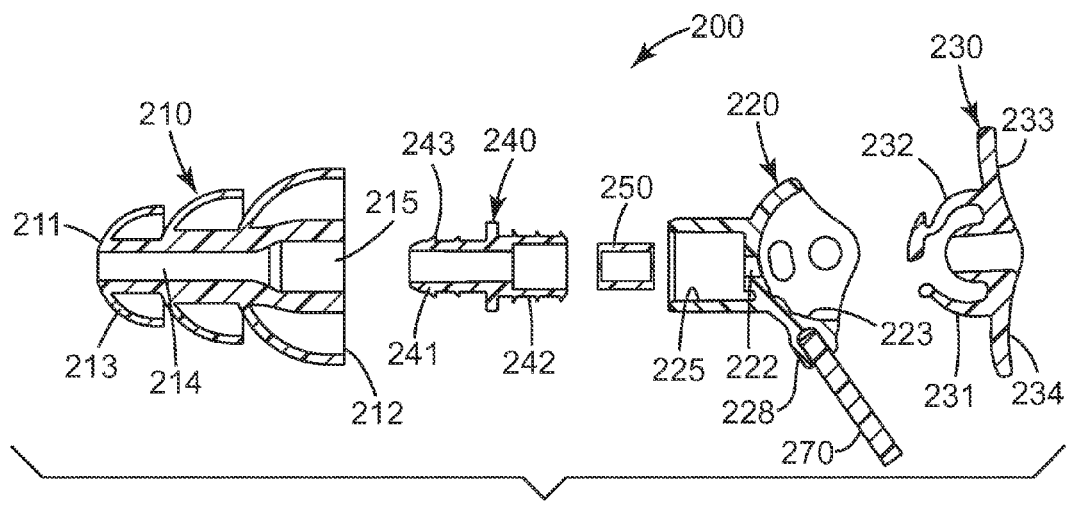
FIG. 2 is an exploded cross-sectional view of a selective attenuating earplug according to an exemplary embodiment of the present invention.

FIG. 2 provides an exploded sectional view of an exemplary embodiment of a selective attenuating earplug 200. Earplug 200 includes a sound attenuating tip 210 having a first end 211 and a second end 212, a body 220, a switch 230, a coupler 240, and one or more filters 250.

Tip 210 is made of soft and pliable foam, rubber, polymer, or other suitable material that may be comfortably positioned in the ear canal of a user. In an exemplary embodiment, tip 210 at least partially conforms to the ear canal of a user to provide a sufficient acoustic or pneumatic seal against the walls of the ear canal. In various exemplary embodiments, tip 210 is made of a styrene ethylene butylene styrene (SEBS) thermoplastic elastomer (TPE), such as C-FLEX available from Consolidated Polymer Technologies, Inc. of Clearwater, Fla. Other suitable materials include silicone, polyurethane foam or other suitable materials as known in the art.

In an exemplary embodiment, tip 210 includes a plurality of flanges 213 that may flex when a portion of tip 210 is positioned in an ear canal. In various other exemplary embodiments, tip 210 may be bullet-shaped, bell-shaped, cone-shaped, mushroom-shaped, or otherwise shaped to provide a desired fit or to suit a particular application.

Exemplary earplug 200 further includes a body 220 having a cavity 225, an aperture 222, and a curved inner surface 223. Switch 230 is positioned partially within body 220 and may be toggled between two or more positions.

Tip 210 may be attached to body 220 directly or indirectly. In an exemplary embodiment illustrated in FIG. 2, tip 210 and body 220 include cavities 215 and 225, respectively, to accommodate first and second ends 241 and 242 of a connector, such as coupler 240. Cavities 215 and 225 and first and second ends 241 and 242 of coupler 240 may be sized such that an interference fit is achieved and coupler 240 frictionally retains tip 210 and body 220 on coupler 240. In various exemplary embodiments, coupler 240 and/or tip 210 and body 220 include mating features 243 such as barbs, ribs, projections, and/or complementary features that serve to retain tip 210 or body 220 on coupler 240.

In an exemplary embodiment, tip 210 and/or body 220 are removably coupled to coupler 240 such that the tip 210 and body 220 can be disassembled from coupler 240, such as to replace tip 210 or other components. Tip 210, for example may be replaced due to wear, soiling, or to select a different size or style to provide a desired fit or functionality. In various other exemplary embodiments, tip 210 and/or body 220 may be adhesively bonded, integrally formed, or otherwise permanently joined to coupler 240. In alternative exemplary embodiments, tip 210 and body 220 include respective complementary shapes that allow tip 210 to be attached directly to body 220 without an independent coupler. For example, an exemplary body may include a projection configured to be accommodated in a cavity of tip 210, or vice versa, or tip 210 and body 220 may be attached as a result of being integrally formed in an injection molding process, for example.

When assembled, body 220 provides sufficient rigidity that earplug 200 may be positioned for use at least partially in the ear of a user by pushing tip 210 into the ear canal with an appropriate force. That is, a body 220 having sufficient rigidity or stiffness combined with an appropriate tip 210 allows earplug 200 to be positioned for use at least partially in the ear of a user without the need to first compress or "roll down" tip 210. Direct insertion without the need to first compress or "roll down" tip 210, for example, promotes hygiene by limiting contact with tip 210 prior to placement in the ear.

Body 220 is made of a relatively rigid polymer or other suitable material having sufficient rigidity or stiffness. In an exemplary embodiment, body 220 is made of a polyamide (PA), such as ZYTEL available from DuPont. Other suitable materials include polyethylene terephthalate (PET), polyoxymethylene (POM), or other suitable materials as known in the art. In some exemplary embodiments, body 220 and switch 230 are made from a similar or identical material. In other exemplary embodiments, body 220 is made of a PA while switch 230 is made of a POM, such as DELRIN available from DuPont.

In an exemplary embodiment, body 220 includes a recess, loop, aperture, or other suitable feature, such as cavity 228, for attaching a cord 270. Cord 270 includes first and second ends that may be attached to first and second earplugs, respectively. In an exemplary embodiment, cord 270 exhibits a dull or matte finish to minimize reflection of light.

Earplug 200 includes a passageway, such as acoustic channel 214, extending from aperture 222 of body 220 to the first end 211 of tip 210. Acoustic channel 214 thus passes through coupler 240, if present. Acoustic channel 214 provides an air passageway between aperture 222 and the first end of tip 210. Acoustic channel 214 thus allows sound waves entering acoustic channel 214 through aperture 222 from an external environment to travel to an ear canal of a user when earplug 200 is positioned for use and switch 220 is positioned such that aperture 222 is at least partially unobstructed. In various exemplary embodiments, channel 214 may have a uniform diameter or a varying diameter along its length, may curve, and/or may exhibit various regular or irregular shapes and sizes.

Sound travelling through channel 214 passes through the one or more acoustic filters 250. In an exemplary embodiment, the one or more acoustic filters 250 may include one or more relatively narrow apertures that selectively allow passage of sound waves. For example, the one of more filters 250 may be configured with a narrow aperture that increases the attenuation of sound above a predetermined intensity. In an exemplary embodiment, one or more filters 250 may include one or more filters as described in U.S. Pat. Nos. 6,148,821, 6,070,693, 6,068,079, or 5,936,208 for example, incorporated herein by reference in their entirety.

Exemplary switch 220 is adjustable between a first position in which the aperture is at least partially open to allow passage of sound through aperture 222 and acoustic channel and a second position in which aperture 222 is blocked. An exemplary earplug 200 includes a switch having one or more integral cantilever spring arms that are biased against a surface of the body and interact with one or more features on a surface of the body to maintain the switch in the first position or the second position. Referring to FIG. 2, switch 230 includes first and second cantilever spring arms 231 and 232, and first and second activation levers 233 and 234. Cantilever spring arms 231 and 232 extend in a direction generally away from first and second activation levers 233 and 234. Cantilever spring arms 231 and 232 are generally arcuate or exhibit a desired curvature when assembled with body 220. In some embodiments, one or both of cantilever spring arms 231 and 232 may exhibit little or no curvature before being assembled to body 220, and may curve due to contact with surface 223 or other features of body 220 or earplug 200. In other embodiments, cantilever spring arms 231 and 232 exhibit an initial curvature, and are caused to exhibit a greater curvature upon assembly with body 220 due to contact with surface 223 or other features of body 220 or earplug 200. One or both of cantilever spring arms 231 and 232 function as a spring and are biased against surface 223 due to the natural tendency of cantilever spring arms 231 and 232 to return to an original configuration. Only a slight deformation of cantilever spring arms 231 and 232 may be necessary upon assembly of switch 230 with body 220 to achieve the desired effect. That is, deformation or flexure of cantilever spring arms 231 and 232 when assembled with body 220 will generally remain in the elastic regime.

Figure 3A:
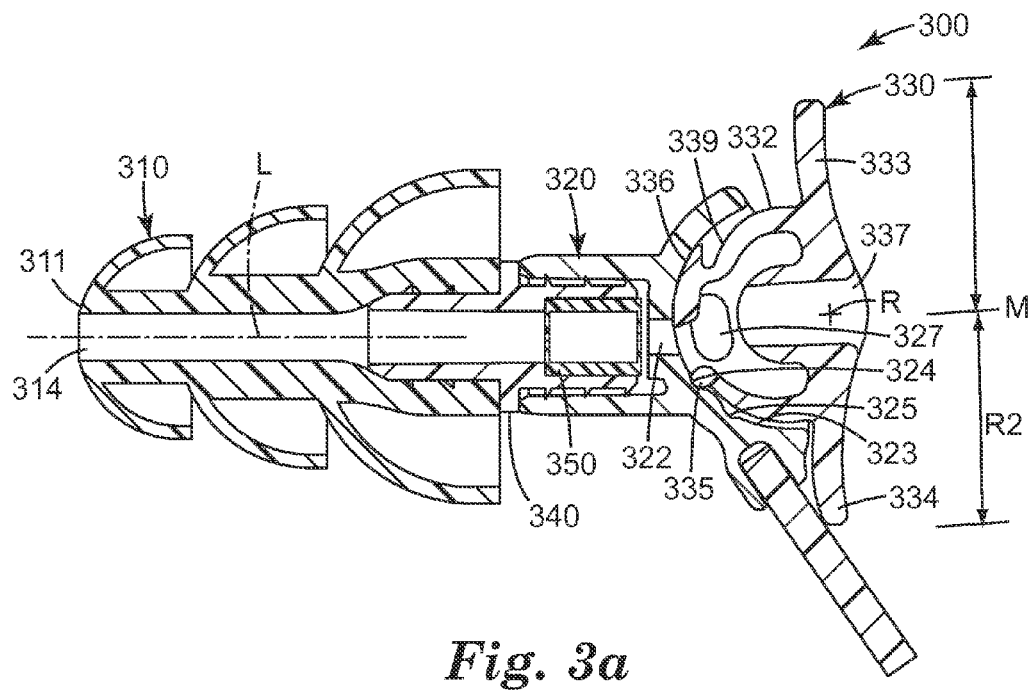
FIG. 3a is a cross-sectional view of a selective attenuating earplug according to an exemplary embodiment of the present invention in which a switch is in a first position.
Figure 3B:
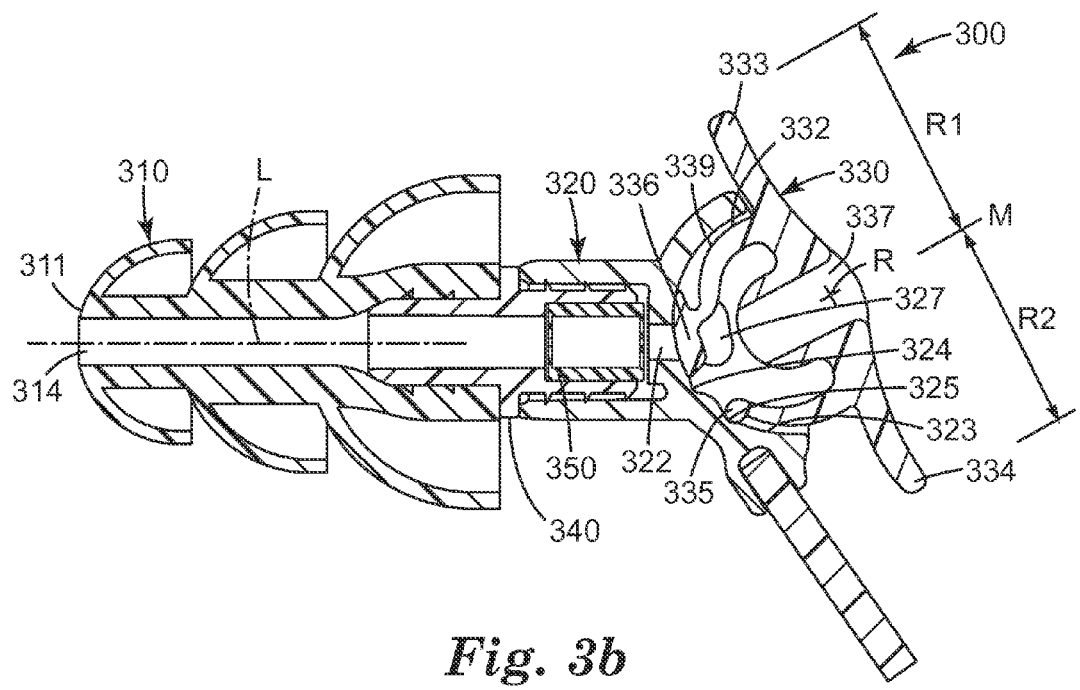
FIG. 3b is a cross-sectional view of a selective attenuating earplug according to an exemplary embodiment of the present invention in which a switch is in a second position.

FIGS. 3a and 3b illustrate an exemplary earplug 300 having a tip 310, a body 320, and a switch 330 in a first position (FIG. 3a) and a second position (FIG. 3b). Earplug 300 includes a channel 314 extending from aperture 322 of body 320 to first end 311 of tip 310. When switch 330 is positioned such that aperture 322 is at least partially unobstructed, channel 314 allows sound waves entering aperture 322 from an external environment to travel to an ear canal of a user.

Switch 330 includes a first cantilever spring arm 331 having a shape, such as cam lobe or protrusion 335, that interacts with one or more features, such as first and second recesses 324 and 325, on surface 323 of body 320 to maintain switch 330 in a first or second position, respectively. In a first position illustrated in FIG. 3a, protrusion 335 is positioned in recess 324. As described above with reference to earplug 200, at least an end portion of first cantilever spring arm 331 is biased towards surface 323 and recess 324 by a spring force resulting from the flexure of first cantilever spring arm 331. The spring force may result from the original curvature of first cantilever spring arm 331 and/or flexure or deformation of the first cantilever spring arm 331 when assembled with body 320. In this way, protrusion 335 is maintained in recess 324.

In a first position illustrated in FIG. 3a, aperture 322 is at least partially unobstructed such that sound waves may enter aperture from the external environment. Sound waves may travel into body 320 through openings or ports in body 320, such as port 327, or one or more openings or ports 337 in switch 330, or through openings between body 320 and switch 330. Sound waves entering aperture 322 encounter one or more filters 350 and may be attenuated based on the performance of filter 350. In an exemplary embodiment, one or more filters 350 include two or more small openings. Sound waves passing through filter 250 are selectively attenuated such that high intensity sounds are attenuated, while sounds below a specified intensity or within a desired frequency range pass with little or no attenuation.

In a second position illustrated in FIG. 3b, aperture 322 is blocked by sealing pad 336 proximate an end of second cantilever spring arm 332. Similar to first cantilever spring arm 331 described above, the sealing pad of second cantilever spring arm 332 is biased towards aperture 322 and/or surface 323 of body 320 by a spring force resulting from the flexure of second cantilever spring arm 332. The spring force may result from the original curvature of second cantilever spring arm 332 and/or flexure or deformation of the second cantilever spring arm 332 when assembled with body 320. In this way, sealing pad 336 is pushed against a perimeter of aperture 322 and blocks aperture 322 to prevent sound waves from the external environment from entering sound channel 314.

The configuration of a sealing pad proximate an end of cantilever spring arm 332 provides several advantages in blocking aperture 322. When moving between a first position to a second position, sealing pad 336 moves across aperture 322, as opposed to being inserted into or removed from aperture 322, for example. The spring force provided by second cantilever spring arm 332, for example, biases the sealing pad 336 against aperture 322 and a perimeter of aperture 322 and ensures an appropriate seal such that aperture 322 is completely or nearly completely blocked. Due to the spring force of second cantilever spring arm 332, an appropriate seal may be maintained even if sealing pad 336, body 320 or other components of earplug 300 change shape or are eroded due to wear from repeated operation of switch 330. Additionally, certain manufacturing tolerances need not be particularly precise because sealing pad 336 does not need to be precisely positioned to create an interference fit, for example, as might be required if it were inserted into aperture 322 as a plug.

In an exemplary embodiment, second cantilever spring arm 332 includes an articulation portion 339 proximate sealing pad 336. Articulation portion 339 allows for articulation of sealing pad 336 such that sealing pad 336 may articulate or rotate to provide a better seal over aperture 322. In various exemplary embodiments, articulation portion 339 may include a portion or area of second cantilever spring arm 332 having a reduced diameter or thickness or may include a stepped portion. In some exemplary embodiments, articulation portion 339 provides an additional biasing force to bias sealing pad 336 towards aperture 322 to ensure an appropriate seal.

Switch 330 may be toggled between a first position, as illustrated in FIG. 3a, and a second position, as illustrated in FIG. 3b, by application of appropriate force on first activation lever 333 or second activation lever 334. Application of an appropriate force on first activation lever 333 when switch 330 is in a first position results in first cantilever spring arm 331 flexing as protrusion 335 slides out of first recess 324. Protrusion 335 and/or sealing pad 336 follows a generally arcuate path as switch 330 rotates from a first position to a second position in which protrusion 335 reaches second recess 325. The spring force of first cantilever spring arm 331 biases protrusion 335 into second recess 325 to maintain switch 330 in a second position illustrated in FIG. 3b. Switch 330 is thus maintained in a second position until an appropriate force is applied to second activation lever 334 to toggle switch 330 to a first position. A stop may be provided to prevent over rotation of switch 330. In an exemplary embodiment, first and second recesses 324 and 325 are positioned such that when protrusion 335 is maintained in first or second recesses one of the first or second activation levers 333, 334 are in close proximity to an edge of body 320 such that additional rotation of switch 330 is limited or prevented.

In an exemplary embodiment, an indication is provided to a user when the earplug is switched between a first position and a second position. For example, a switching between a first position may provide an audible indication, such as a click or snap. First and second audible indications may be provided when switch 330 is toggled from a first position to a second position and a second position to a first position, respectively. The first and second audible indications may be similar, or may be dissimilar so as to provide an indication that the switch is in a particular position. In various other indications, a tactile indication may be provided as the switch 330 is toggled to a first or second position, to provide an indication to the user that the switch is in a particular position.

When toggled between first and second positions, switch 330 and sealing pad 336 rotate about an axis that is not parallel to a longitudinal axis of tip 310. In the exemplary embodiment of FIGS. 3a and 3b, switch 330 rotates about an axis R that is perpendicular to a longitudinal axis L of tip 310. A switch rotating about an axis perpendicular to a longitudinal axis of tip 310 is believed to provide ergonomic advantages allowing easy operation of switch 330 while earplug 300 is positioned in an ear of a user. Further, such operation allows first and second activation levers 333 and 334 to extend on either side of the axis of rotation to facilitate operation of switch 330. For example, relatively large first and second activation levers 333 and 334 may allow easy operation of switch 330, and may allow operation even when a user is wearing gloves, for example. In various exemplary embodiments, outer edges 333a and 334a of first and second activation levers 333 and 334 may extend distances R1 and R2, respectively, from a midpoint M of switch 330 between approximately 4 mm and 20 mm, 6 mm and 16 mm, or between approximately 8 and 12 mm.

In some embodiments, tip 310 and body 320 share a longitudinal axis L. In various other embodiments, body 320, coupler 340 or other portion of earplug 300 may be curved or angled, for example, such that at least a portion of body 320, coupler 340, or other portion of earplug 300 exhibit a second longitudinal axis (not shown) that is different from, or angled relative to, longitudinal axis L. In various exemplary embodiments, the axis of rotation R is similarly not parallel to the second longitudinal axis.

Figure 4:
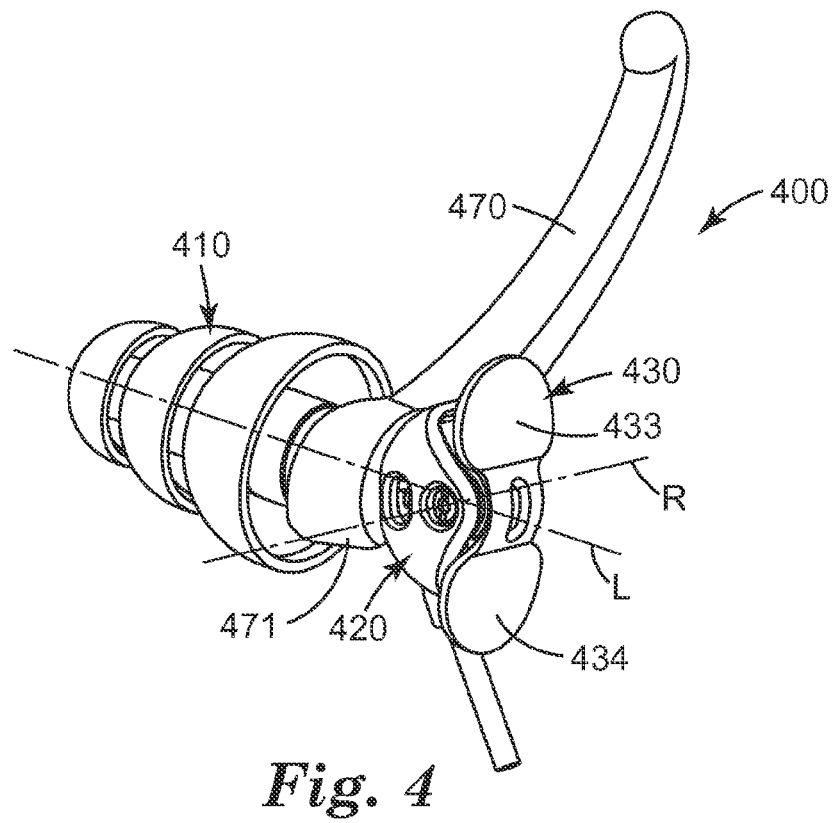
FIG. 4 is a perspective view of a selective attenuating earplug according to an exemplary embodiment of the present invention including a retainer device.

FIG. 4 illustrates an exemplary earplug 400 similar to exemplary earplugs 100, 200, and 300 described above and including a retainer 470. Retainer fits in the concha, for example, of a user's ear and provides additional security of earplug 400 in the ear of a user. Earplug 400 is securely maintained in position by interference between tip 410 and the ear canal of a user and the friction between retainer 470 and the concha or other portions of a user's ear.

In an exemplary embodiment, retainer 470 is secured to body 420 by an aperture or loop 471 that a portion of body 420 passes through. The retainer 470 may be attached to the body by sliding retainer 470 on or off of body 420 when tip 410 is not attached to body 420. When tip 410 is attached to body 420, removal of retainer 470 is prevented. In some embodiments, retainer 470 may rotate and/or slide relative to body 420 or tip 410. Thus, the position of retainer 470 may be adjusted to provide a comfortable fit for a range of users.

As described above with reference to earplug 300, switch 430 rotates about an axis R that is not parallel to the longitudinal axis L of tip 410 when switch 430 is toggled between a first and second position. When toggled between first and second positions, switch 430 and a sealing pad (not shown) rotate about an axis that is not parallel to a longitudinal axis of tip 410. In the exemplary embodiment of FIG. 4, switch 430 rotates about an axis R that is perpendicular to a longitudinal axis L of tip 410. A switch rotating about an axis perpendicular to a longitudinal axis of tip 410 is believed to provide ergonomic advantages allowing easy operation of switch 430 while earplug 400 is positioned in an ear of a user. Further, such operation allows first and second activation levers 433 and 434 to extend on either side of the axis of rotation to facilitate operation of switch 430.

Figure 5:
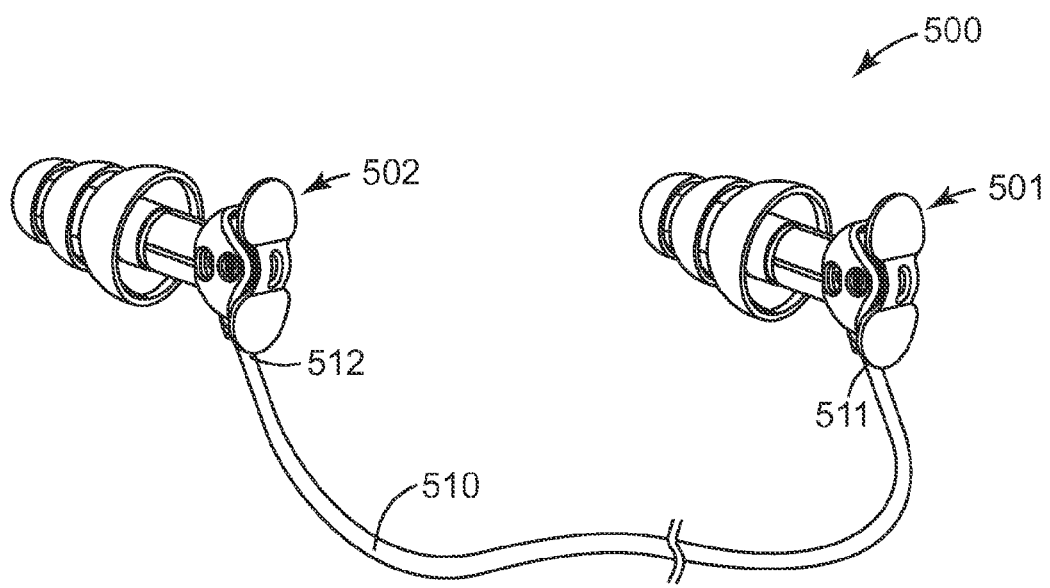
FIG. 5 provides a perspective view of a hearing protection device according to the present invention.

FIG. 5 provides a perspective view of a hearing protection device 500 according to the present invention. Hearing protection device 500 includes first and second selective attenuating earplugs 501 and 502 having features and characteristics as described herein. First and second selective attenuating earplugs 501 and 502 are joined by a cord 510 having first and second ends 511, 512.

The present invention has now been described with reference to several embodiments thereof. The foregoing detailed description has been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the exact details described herein, but rather by the language of the claims and the equivalents thereof. Any feature or characteristic described with respect to any of the above embodiments can be incorporated individually or in combination with any other feature or characteristic, and are presented in the above order and combinations for clarity only.

What is claimed is:

1. A selective attenuating earplug, comprising:
a tip extending between a first end and a second end along a longitudinal axis;
a body attached to the tip proximate the second end such that the body is closer to the second end of the tip than the first end of the tip, and comprising an aperture in a wall of the body;
an acoustic channel extending from the first end of the tip to the aperture along the longitudinal axis; and
a switch adjustable between a first position in which the aperture is at least partially open to allow passage of sound through the aperture and the acoustic channel and a second position in which the aperture is blocked;
wherein the switch comprises a first cantilever spring arm including a shape that is biased against a surface of the body and that interacts with one or more features on the surface of the body to maintain the switch in the first position, wherein the shape of the first cantilever spring arm includes a protrusion and the one or more features comprise first and second recesses, and the protrusion interacts with the first recess on the surface of the body to maintain the switch in the first position and interacts with the second recess on the surface of the body to maintain the switch in the second position.

2. The selective attenuating earplug of claim 1, wherein the tip and the body are integrally formed.

3. The selective attenuating earplug of claim 1, wherein the protrusion of the first cantilever spring arm follows an arcuate path when switched between the first position and the second position.

4. The selective attenuating earplug of claim 1, wherein the first cantilever spring arm is curved when the switch is in the first position or the second position.

5. The selective attenuating earplug of claim 1, wherein the switch rotates about an axis that is not parallel to the longitudinal axis of the tip.

6. The selective attenuating earplug of claim 1, wherein the switch further comprises a sealing pad that blocks the aperture when the switch is in the second position.

7. The selective attenuating earplug of claim 6, wherein the switch further comprises a second cantilever spring arm and the sealing pad is integrally formed with the second cantilever spring arm.

8. The selective attenuating earplug of claim 6, wherein the sealing pad moves across the aperture when switched between the first position and the second position.

9. The selective attenuating earplug of claim 1, further comprising a cord coupled to the body.

10. The selective attenuating earplug of claim 1, wherein the tip comprises one or more flanges.

11. The selective attenuating earplug of claim 1, wherein an acoustic filter is positioned in the acoustic channel.

12. The selective attenuating earplug of claim 1, further comprising a connector having a first end positioned in a cavity of the second end of the tip and a second end positioned in a cavity of the body, the acoustic channel extending through the connector.

13. A hearing protection device, comprising:
first and second selective attenuating earplugs joined by a cord, wherein each of the first and second selective attenuating earplugs comprises a tip extending between a first end and a second end along a longitudinal axis; a body attached to the tip proximate the second end such that the body is closer to the second end of the tip than the first end of the tip; an acoustic channel extending from a first end of the tip to an aperture of the body along the longitudinal axis; and a switch adjustable between a first position in which the aperture is at least partially open to allow passage of sound through the aperture and the acoustic channel and a second position in which the aperture is blocked; wherein the switch comprises a first cantilever spring arm including a shape that is biased against a surface of the body and that interacts with one or more features on the surface of the body to maintain the switch in the first position, wherein the shape of the first cantilever spring arm includes a protrusion and the one or more features comprise first and second recesses, and the protrusion interacts with the first recess on the surface of the body to maintain the switch in the first position and interacts with the second recess on the surface of the body to maintain the switch in the second position.

* * * * *